United States Patent
McChesney et al.

(10) Patent No.: US 12,265,074 B2
(45) Date of Patent: Apr. 1, 2025

(54) BOREHOLE ELECTROKINETIC ENERGY GENERATION AND ON-LINE WATER DETERMINATION

(71) Applicant: Halliburton Energy Services, Inc., Houston, TX (US)

(72) Inventors: Ryan W. McChesney, Carrollton, TX (US); Michael Linley Fripp, Singapore (SG); Stephen Michael Greci, Carrollton, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 105 days.

(21) Appl. No.: 18/344,691

(22) Filed: Jun. 29, 2023

(65) Prior Publication Data

US 2025/0003947 A1    Jan. 2, 2025

(51) Int. Cl.
*E21B 47/113* (2012.01)
*E21B 34/06* (2006.01)
*E21B 49/08* (2006.01)
*G01N 33/28* (2006.01)

(52) U.S. Cl.
CPC ....... *G01N 33/2847* (2013.01); *E21B 34/066* (2013.01); *E21B 47/113* (2020.05); *E21B 49/081* (2013.01); *E21B 49/0875* (2020.05)

(58) Field of Classification Search
CPC ............ E21B 47/113; E21B 49/0875
See application file for complete search history.

(56) References Cited

U.S. PATENT DOCUMENTS

| | | | |
|---|---|---|---|
| 7,944,211 B2 | 5/2011 | Smits | |
| 8,508,741 B2 | 8/2013 | Kumar | |
| 2018/0163537 A1 | 6/2018 | Rahaliou et al. | |
| 2018/0313192 A1 | 11/2018 | Frosell et al. | |
| 2019/0010783 A1 | 1/2019 | Frosell et al. | |
| 2019/0225902 A1* | 7/2019 | Aljindan | F17D 1/04 |
| 2019/0368664 A1 | 12/2019 | Wu et al. | |
| 2023/0408309 A1* | 12/2023 | Huang | G01F 15/063 |

FOREIGN PATENT DOCUMENTS

WO    2013169234 A1    11/2013

* cited by examiner

*Primary Examiner* — Giovanna Wright
(74) *Attorney, Agent, or Firm* — Scott Richardson Parker Justiss, P.C.

(57) ABSTRACT

A fluid flow control device, a well system, and a method are provided. The fluid flow control device, in one aspect, may include an inlet port, allowing a downhole fluid of a borehole to flow into the fluid flow control device, and an outlet port, allowing the downhole fluid to flow out of the fluid flow control device. The fluid flow control device, in accordance with this aspect, may further include a fluid chamber positioned between the inlet port and the outlet port, wherein an electrokinetic film is located within the fluid chamber and is capable of generating a voltage as the downhole fluid flows over the electrokinetic film.

24 Claims, 11 Drawing Sheets

BOREHOLE ELECTROKINETIC ENERGY GENERATION AND ON-LINE WATER DETERMINATION

TECHNICAL FIELD

This application is directed, in general, to monitoring fluid flow of a borehole and, more specifically, to using the electrokinetic effect within a fluid line.

BACKGROUND

Wellbores are sometimes drilled from the surface of a wellsite several hundred to several thousand feet downhole to reach hydrocarbon resources. During certain well operations, such as production operations, certain fluids, such as fluids of hydrocarbon resources, are extracted from the formation. For example, the fluids of hydrocarbon resources may flow into one or more sections of a conveyance, such as a section of a production tubing, and through the production tubing, uphole to the surface. During production operations, other undesirable types of fluids, such as water, sometimes also flow into the section of production tubing while the fluids of hydrocarbon resources are being extracted. It would be beneficial to detect or separate the undesirable fluids.

SUMMARY

In one aspect, a fluid flow control device for use with a downhole tool located in a borehole is disclosed. In one embodiment, the fluid flow control device, includes (1) an inlet port, allowing a downhole fluid of the borehole to flow into the fluid flow control device, (2) an outlet port, allowing the downhole fluid to flow out of the fluid flow control device, and (3) a fluid chamber positioned between the inlet port and the outlet port, wherein an electrokinetic film is located within the fluid chamber and is capable of generating a voltage as the downhole fluid flows over the electrokinetic film, and a voltage parameter can be determined from the generated voltage.

In a second aspect, a well system is disclosed. In one embodiment, the well system includes (1) a borehole formed through a subterranean formation. (2) a tubing string positioned within the borehole, and (3) a fluid flow control device coupled to the tubing string, the fluid flow control device including (a) an inlet port, allowing a downhole fluid of the borehole to flow into the fluid flow control device. (b) an outlet port, allowing the downhole fluid to flow out of the fluid flow control device, and (c) a fluid chamber positioned between the inlet port and the outlet port, wherein an electrokinetic film is located within the fluid chamber and is capable of generating a voltage as the downhole fluid flows over the electrokinetic film.

In a third aspect, a method is disclosed. In one embodiment, the method includes (1) positioning a fluid flow control device coupled to tubing string within a borehole formed through a subterranean formation, the fluid flow control device including (a) an inlet port, allowing a downhole fluid of the borehole to flow into the fluid flow control device, (b) an outlet port, allowing the downhole fluid to flow out of the fluid flow control device, (c) a fluid chamber positioned between the inlet port and the outlet port, wherein an electrokinetic film is located in an interior of the fluid chamber and is capable of generating a voltage as the downhole fluid flows over the electrokinetic film, and (d) an electronics system able to determine one or more voltage parameters at one or more measuring locations within the fluid chamber using the generated voltage, (2) analyzing the one or more voltage parameters using the electronics system, and (3) determining a one or more downhole fluid characterizations using the one or more voltage parameters.

BRIEF DESCRIPTION

Reference is now made to the following descriptions taken in conjunction with the accompanying drawings, in which.

DETAILED DESCRIPTION

Figure 1:
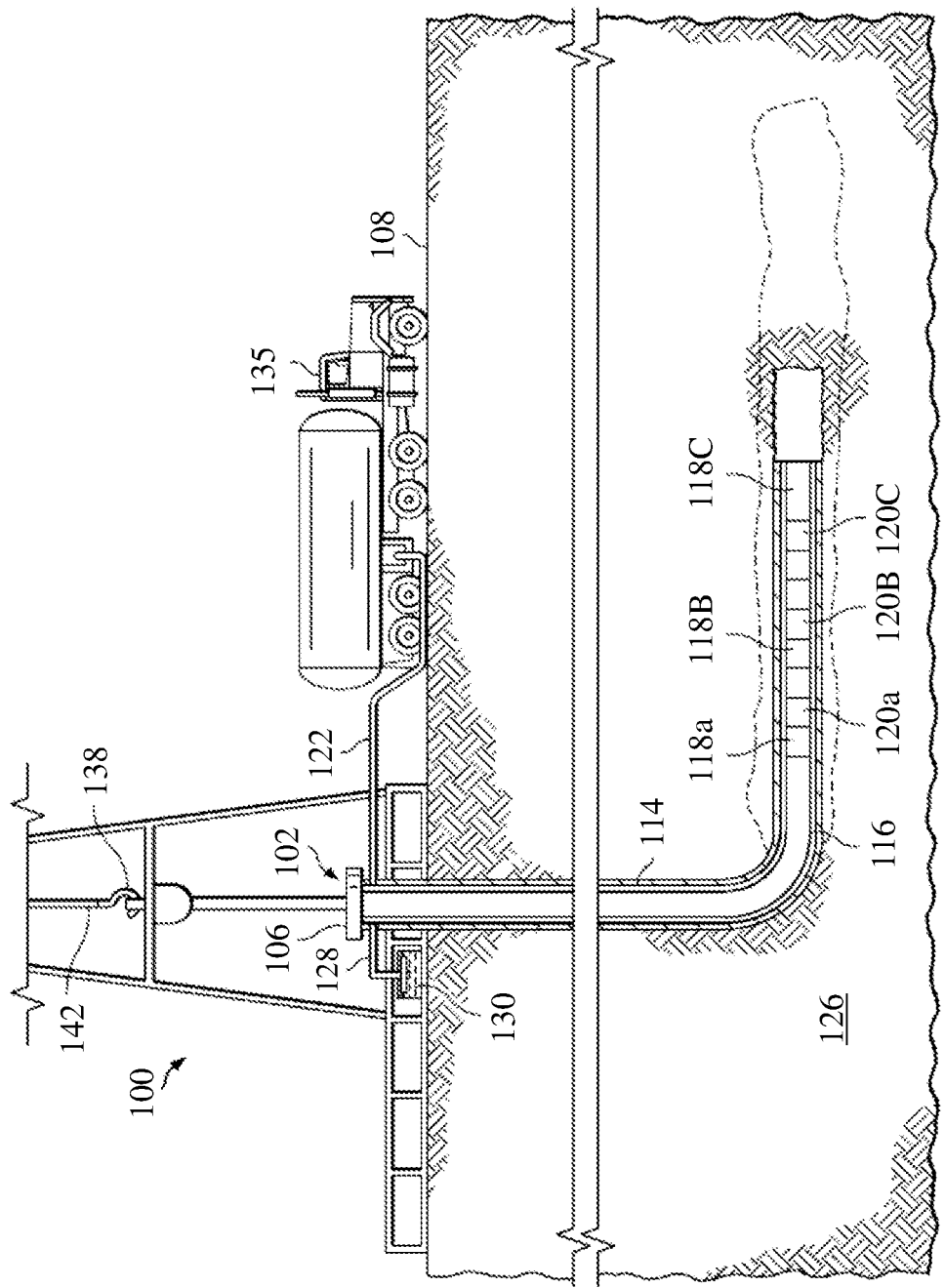
FIG. 1 is an illustration of a diagram of an example schematic side view of a well system.

In a hydrocarbon well system, fluid can be extracted or pumped from a downhole location of a borehole toward a surface location. Hydrocarbons can be oil, gas, other desirable products found in a subterranean formation. As the hydrocarbons are extracted from a reservoir, a fracturing environment, or otherwise pumped to the surface, other fluids can mix with the hydrocarbons. For example, water from the subterranean formation can mix with the hydrocarbons, making the hydrocarbons less valuable as the water would need to be separated out at a later time of the production cycle. In some borehole systems, there can be more than one location within the borehole where the hydrocarbons can be extracted from the reservoir or subterranean formation. When a water level, i.e., a water cut or an on-line water determination (OWD), exceeds a certain amount, it can be beneficial to shut off hydrocarbon extraction or pumping from that location, and continue operations at the other extraction or pumping locations. Water, as used herein, can be water, brine, or other combinations and solutions that include water.

In well systems, there can be a fluid flow control device located within the borehole to control the flow of fluids. In some aspects, the fluid flow control device may be an inflow control device (ICD). In some aspects, the ICD can be autonomous (AICD). In some aspects, the ICD can be an electronic ICD (eICD). The fluid flow control device, in some aspects, includes an inlet port to allow downhole fluid to enter the fluid flow control device. In some aspects an outlet port can be present to allow downhole fluid to exit the fluid flow control device. Conventional fluid flow devices used in borehole operations may not have the ability to detect the composition of the fluid being produced. Downhole fluids can be one or more of a gas, an oil, a water, a brine, a drilling mud, a fracturing fluid, an injection fluid, other fluids found in the borehole or subterranean formation, or other fluids pumped into the borehole.

In the present disclosure, an apparatus and well system are presented that allow a fluid flow control device, such as an autonomous inflow control device (AICD), electronic inflow control device (eICD), etc., to detect OWD and to open or close valves using the detected composition of the fluid. The fluid flow control device can have one or more valves, e.g., a valve set, which can be controlled to open, allowing the downhole fluid to pass through, or to close, stopping the downhole fluid from passing through. In some aspects, the valves can be located at or near the inlet port, the outlet port, other ports, or a combination thereof.

Between the inlet port and the outlet port can be a pathway or fluid chamber which allows the downhole fluid to flow through the fluid chamber. In some aspects, on an interior surface of the pathway or fluid chamber, an electrokinetic film can be located allowing the downhole fluid to pass over the film. The electrokinetic film can be electrically coupled to an electronics system. In some aspects, the electrokinetic film can be axially or circumferentially lengthened, folded, positioned within the interior of the fluid chamber in various orientations, or otherwise configured to increase the surface area of the electrokinetic film exposed to the downhole fluid flow as compared to the interior surface area of the fluid chamber.

The electronics system can harvest electrical energy (e.g., an energy capture system) and direct its usage toward charging batteries, charging capacitors, or be used by a device such as one or more valve motors. The batteries and capacitors can be an energy storage system. The electronics system can detect voltage changes received from the electrokinetic film and analyze the voltage changes to determine downhole fluid characteristics, such as a percentage of water, a water cut threshold, or a downhole fluid flow rate, among others. The electronic system can determine a voltage parameter that describes the characterizations. For example, as a bubble of water passes a first and then a second voltage sensor coupled to the electrokinetic film, the changes in voltages detected across the one or more measuring locations, such as when the oil, then water bubble, then oil passes over each sensor, can be used to determine the downhole fluid characterizations, for example including fluid flow rate.

In some aspects, the fluid flow control device can be used to generate energy, such as using the electrokinetic effect, for example, using an energy generation system to harvest the electrical energy. The electrokinetic effect can convert kinetic energy of an electrolyte fluid flow into electrical energy, such as having the downhole fluid pass over the electrokinetic film. In some aspects, an oxide film can be used such that as water or a water solution flows over the oxide film, a voltage can be detected (e.g., the generated voltage). In some aspects, the oxide film can be an iron oxide film or other type of oxide film, such as vanadium or nickel. The preferred metal oxide contains a intraoxide electron transfer because the thermal oxides contain several metal-oxidation states. For example, aluminum oxide and chromium oxide do not support intraoxide electron transfer and exhibit dramatically reduced performance. In some aspects, the oxide film can be a graphene layer. In some embodiments, the electrokinetic film is applied through a physical vapor deposition process. In one example, a 10-nm-thick iron layer is applied and the iron reacts with air to form a rust-coated iron layer.

Note that the electrokinetic effect is not the result of a chemical reaction between the fluid and the electrokinetic film but is instead the conversion of the kinetic energy of the flow fluid into electricity through a process of ion adsorption and desorption. The ions present in the fluid, such as dissolved salts in water, will attract electrons from the metal beneath the metal oxide in the electrokinetic film. The ions move as the fluid flows and this movement will also drag the electrons in the electrokinetic film. The movement of the electrons generates an electric current.

The amount of voltage can vary in proportion to the amount of water contained within the fluid. For example, oil can be pumped through the fluid flow control device and as the percentage of water versus the oil increases in the fluid flow, the voltage can also increase. The change in voltage can be analyzed and used to determine the percentage of water in the fluid flow. In some aspects, once the percentage of water in the fluid flow is known, then actions can be taken, such as opening or closing one or more valves of the fluid flow control device.

The amount of energy, e.g., electrical energy, generated by the electrokinetic effect is proportional to the surface area of the oxide film. By increasing the oxide film surface area over which the fluid flow passes, increased energy can be achieved to supply energy to other devices, such as one or more control valves of the fluid flow control device. In some aspects, the energy generation described herein can replace the conventional turbine generators used in current fluid flow control devices, thereby reducing the number of moving parts.

In some aspects, a sensor can be deployed to detect OWD, and other fluid characterizations, utilizing the electrokinetic effect. In this aspect, the sensor does not need a moving part, thereby simplifying the sensor and maintenance. The use of the electrokinetic effect for use as a sensor for fluid characterization or energy generation can be utilized in real-time or near real-time by the fluid flow control device or other devices or systems located downhole. For example, the determined voltage parameter can be determined in real-time as the downhole fluid passes over the electrokinetic film and communicated to a system where a decision or action can be initiated. For example, if the voltage parameter indicates the presence of water at a water cut threshold, a valve can be moved to the closed position preventing additional water from entering the system.

In some aspects, the electrokinetic effect can be used in non-production operations. For example, the electrokinetic effect can be used in combination with slickline tools, drilling operations, hydraulic fracturing (HF) operations, or other types of borehole operations. In HF operations, for example, further fracturing fluid can be prevented from being pumped into a location by closing a valve if the fracturing operation detects excess water in the subterranean formation, such as opening a fracture to a water reservoir.

Turning now to the figures, FIG. 1 illustrates a schematic side view of a well system 100 in which fluid flow control devices 120A, 120B, and 120C (collectively, fluid flow control devices 120) can be configured and operated according to the disclosure and are deployed in a borehole 114. Borehole 114 extends from a surface 108 of a well 102 to or through a subterranean formation 126. A hook 138, a cable 142, a traveling block (not shown), and a hoist (not shown) can be provided to lower a conveyance 116 into well 102. As referred to herein, conveyance 116 is any piping, tubular, or fluid conduit including, but not limited to, drill pipe, production tubing, casing, coiled tubing, or any combination thereof. Conveyance 116 provides a conduit for fluids extracted from subterranean formation 126 to travel to surface 108. In some aspects, conveyance 116 provides a conduit for fluids to be conveyed downhole and injected into subterranean formation 126, such as in an injection operation. In some aspects, conveyance 116 can be coupled to a production tubing string that is arranged within a horizontal section of well 102. In FIG. 1, conveyance 116 and the production tubing string are represented by the same tubing.

At a wellhead 106, an inlet conduit 122 is coupled to a fluid source 135 to provide fluids through conveyance 116 downhole. For example, drilling fluids, fracturing fluids, and injection fluids can be pumped downhole during drilling operations, hydraulic fracturing operations, and injection operations, respectively. Fluids can be circulated into well 102 through conveyance 116 and back toward surface 108. A diverter or an outlet conduit 128 can be connected to a container 130 at wellhead 106 to provide a fluid return flow path from borehole 114. Conveyance 116 and outlet conduit 128 can form fluid passageways for fluids, such as hydrocarbon resources to flow uphole during production operations.

Conveyance 116 includes production tubular sections 118A, 118 B, and 118C (collectively, production tubular sections 118) at different intervals adjacent to subterranean formation 126. In some aspects, packers (now shown) can be positioned on the sides of production tubular sections 118 to define production intervals and provide fluid seals between the respective production tubular section 118A, 118B, or 118C, and the wall of borehole 114.

Production tubular sections 118 can include fluid flow control devices 120A-120C. A fluid flow control device can control the volume or composition of the fluid flowing from a production interval into a production tubular section, for example production tubular section 118A. For example, a production interval defined by production tubular section 118A can produce more than one type of fluid component, such as a mixture of oil, water, steam, carbon dioxide, or natural gas.

Fluid flow control device 120A, which is fluidly coupled to production tubular section 118A, reduces or restricts the flow of fluid into the production tubular section 118A. In one or more embodiments, for example wherein the fluid flow control device 120A is an ICD, the fluid flow control device 120A may simply act as a restrictor or orifice to the flow of all fluids. In one or more embodiments, for example wherein the fluid flow control device 120A is an AICD or eICD, the fluid flow control device 120A may reduce or restrict the flow of fluid into the production tubular section 118A based upon the composition of the fluid, such as when the production interval is producing a higher proportion of an undesirable fluid component (e.g., water). Accordingly, this permits the other production intervals that are producing a higher proportion of a desired fluid component (e.g., oil) to contribute more to the production fluid at surface 108 of well 102, so that the production fluid has a higher proportion of the desired fluid component. In some embodiments, the AICD permits or restricts fluid flow into the production tubular sections 118A-118C based upon a composition of the fluid, such as viscosity, density, etc., without requiring signals from the well's surface by the well operator.

In some aspects, fluid flow control devices 120 are an AICD that can permit or restrict fluid flow into the production tubular sections 118 utilizing the sensed fluid characteristics determined from the electrokinetic effect, without requiring signals from the well's surface by a well operator. In some aspects, fluid flow control devices 120 can include a sensor utilizing the electrokinetic effect to determine the OWD. In some aspects, fluid flow control devices 120 can include one or more valves that can be opened or closed depending on the OWD. In some aspects, the valves of fluid flow control devices 120 can be powered by electrical energy generated from the electrokinetic effect.

Although the foregoing paragraphs describe utilizing fluid flow control devices 120A-120C during production, in some aspects, fluid flow control devices 120A-120C can be employed during other types of well operations to control fluid flow through conveyance 116. Further, although FIG. 1 depicts each production tubular section 118A-118C having a fluid flow control device 120A-120C, in some aspects, not every production tubular section 118A-118C has a fluid flow control device 120A-120C. In some aspects, production tubular sections 118A-118C (and fluid flow control devices 120A-120C) can be located in a substantially vertical section additionally or alternatively to the substantially horizontal section of well 102. Further, various numbers of production tubular sections 118A-118C with fluid flow control devices 120A-120C, including one, are deployable in the well 102. In some aspects, while not at common production tubular sections 118A-118C with fluid flow control devices 120A-120C are disposed in simpler boreholes, such as boreholes having a substantially vertical section. In some aspects, fluid flow control devices 120A-120C are located in cased wells or in open-hole environments.

Figure 2:
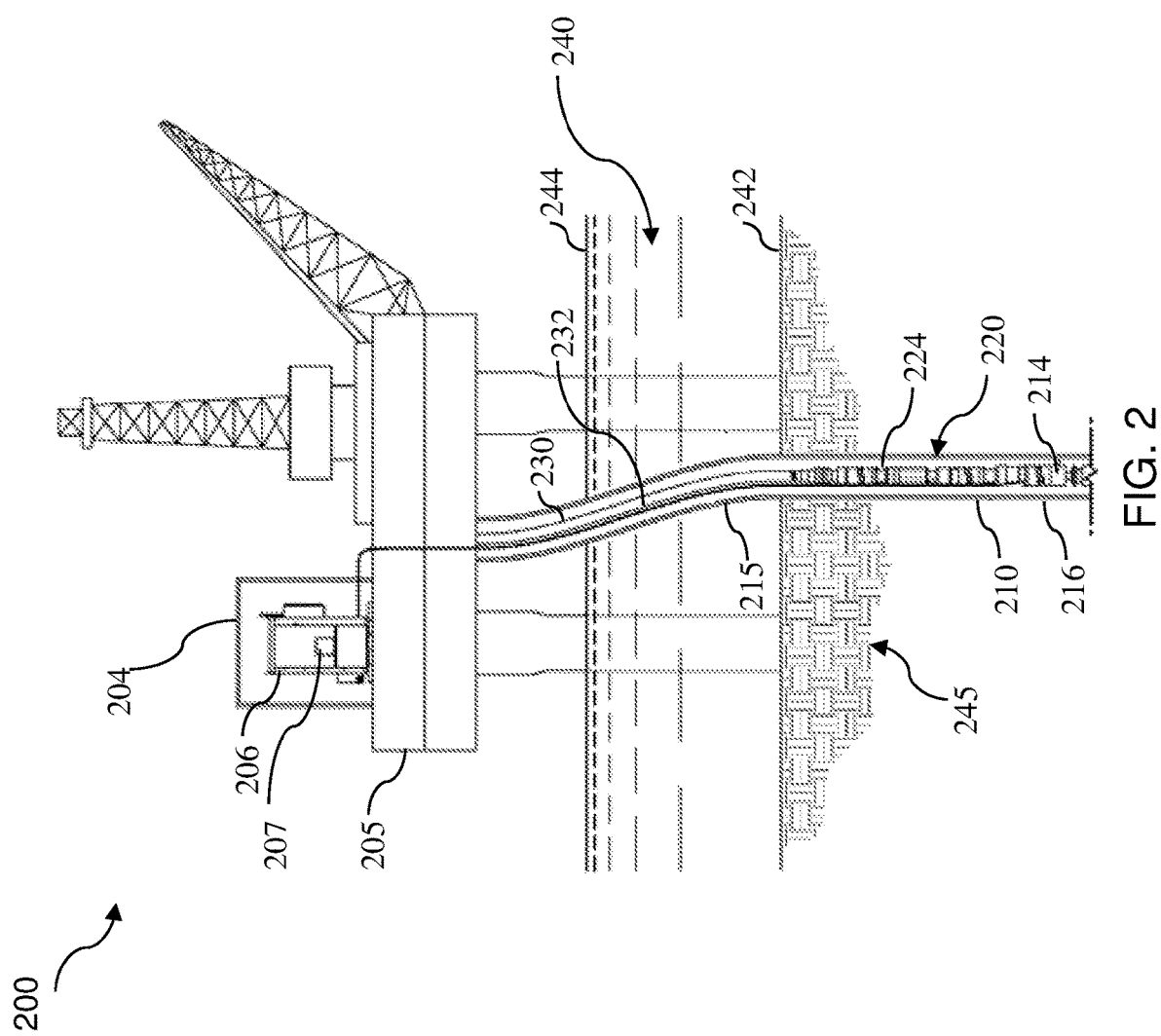
FIG. 2 is an illustration of a diagram of an example offshore well system.

FIG. 2 is an illustration of a diagram of an example offshore well system 200 with an electric submersible pump (ESP) assembly 220. ESP assembly 220 is placed downhole in a borehole 210 below a body of water 240, such as an ocean or sea. Borehole 210, protected by casing, screens, or other structures, is surrounded by subterranean formation 245. ESP assembly 220 can be used for onshore operations. ESP assembly 220 includes a well controller 207 (for example, to act as a speed and communications controller of ESP assembly 220), an ESP motor 214, and an ESP pump 224.

Well controller 207 may be placed in a cabinet 206 inside a control room 204 on an offshore platform 205, such as an oil rig, above water surface 244. Well controller 207 may be configured to adjust the operations of ESP motor 214 to improve well productivity. In the illustrated aspect, ESP motor 214 is a two-pole, three-phase squirrel cage induction motor that operates to turn ESP pump 224. ESP motor 214 is located near the bottom of ESP assembly 220, just above downhole sensors within borehole 210. An energy/communication cable 230 extends from well controller 207 to ESP motor 214. A tubular 232 fluidly couples equipment located on offshore platform 205 and ESP pump 224.

In some aspects, ESP pump 224 can be a horizontal surface pump, a progressive cavity pump, a subsurface compressor system, or an electric submersible progressive cavity pump. A motor seal section and intake section may extend between ESP motor 214 and ESP pump 224. A riser 215 separates ESP assembly 220 from water 240 until sub-surface 242 is encountered, and a casing 216 can separate borehole 210 from subterranean formation 245 at and below sub-surface 242. Perforations in casing 216 can allow the fluid of interest from subterranean formation 245 to enter borehole 210.

One or more electrokinetic effect sensors can be located along ESP assembly 220 where the sensors can use the electrokinetic effect to determine a characterization of the fluid flowing past the sensor. The characterization of the fluid can be used as an input to other processes and systems. In some aspects, the fluid characterization can lead to a change of fluids that are pumped downhole, such as adjusting a composition of a production fluid. In some aspects, the fluid characterization can inform other systems that a change in the pumped fluid composition is to be expected, since the information can reach surface systems prior to the pumped fluid reaching the surface systems. In some aspects, the fluid characterization can be used to control fluid control valves, such as opening one or more valves, closing one or more valves, or a combination thereof.

Fluid characterizations collected from the sensors can be communicated to the electrokinetic fluid flow analyzer. The results can be communicated to one or more other systems, such as well controller 207. Well controller 207 can be the electrokinetic fluid flow analyzer or electrokinetic fluid flow processor, or can be an electrokinetic fluid flow controller. In some aspects, the electrokinetic fluid flow analyzer or electrokinetic fluid flow processor, or the electrokinetic fluid flow controller, can be partially in well controller 207, partially in another computing system, or various combinations thereof.

The results of the electrokinetic fluid flow analyzer, electrokinetic fluid flow processor, or electrokinetic fluid flow controller can be used to generate one or more alerts sent to one or more of a user or a borehole system. For example, an alarm can be specified for a OWD parameter or percentage of the fluid being measured, such as when water exceeds x % of the measured fluid. If the threshold for that OWD parameter is exceeded, then, in some aspects, an alert can be communicated to a user or user group. In some aspects, an alert can be sent to a borehole system to take corrective action. In some aspects, the OWD parameter can be used to issue a command to one or more valves to change its open or closed position, for example, when using an autonomous system.

While FIG. 1 depicts onshore operations, those skilled in the art will understand that the disclosure is equally well suited for use in offshore operations, such as shown in FIG. 2. FIGS. 1-2 depict specific borehole configurations, and those skilled in the art will understand that the disclosure is equally well suited for use in boreholes having other orientations including vertical boreholes, horizontal boreholes, slanted boreholes, multilateral boreholes, and other borehole types. FIGS. 1-2 depict a pumping operation, and those skilled in the art will understand that the disclosure can apply to drilling operations, production operations, intercept operations, relief well operations, completion operations, hydraulic fracturing operations, measure while drilling operations, logging while drilling operations, seismic while drilling operations, completed borehole operations, production testing operations, slickline or wireline operations, coiled tubing string remediation, seismic profiling, and other types of borehole operations without departing from the scope of the disclosure. For example, the disclosure can apply to a drilling borehole system, an injection borehole system, a hydraulic fracturing borehole system, a production borehole system, or a completed borehole system. The borehole operations can be to produce oil or gas products, or for scientific purposes, research, testing, or other non-hydrocarbon related purpose.

Figure 3:
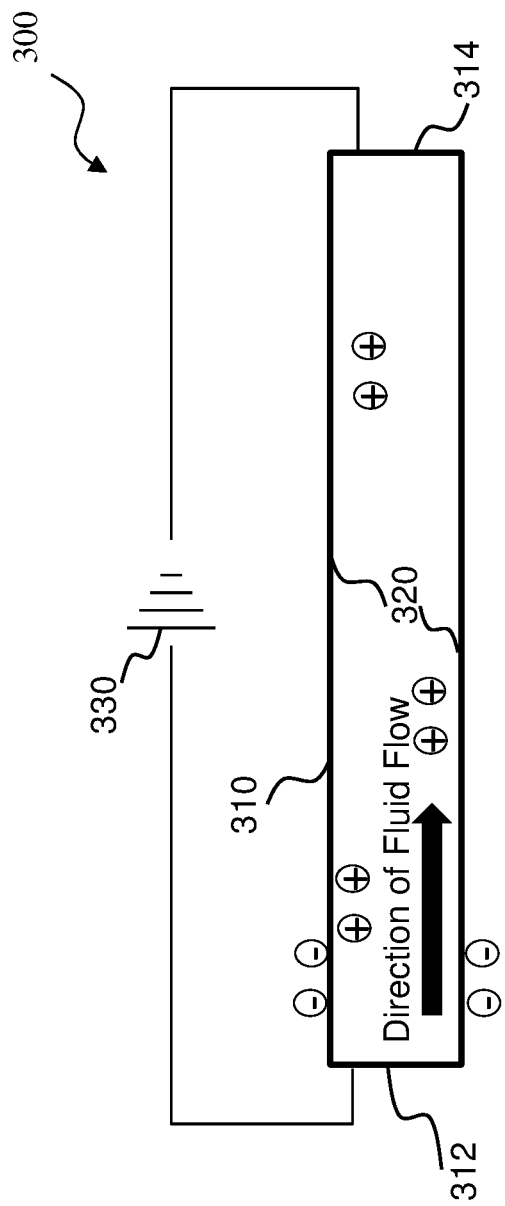
FIG. 3 is an illustration of a diagram of example electrokinetic effect within a fluid line.

FIG. 3 is an illustration of a diagram of example electrokinetic effect 300 within a fluid line. Electrokinetic effect 300 demonstrates a usage of the described process within a borehole of a hydrocarbon well system to detect voltage changes or determine a voltage parameter, from the generated voltage, that can be used for further analysis. Electrokinetic effect 300 includes a fluid pathway or a fluid chamber 310 that is part of a fluid flow control device (not shown). While the term chamber is often discussed herein, unless otherwise stated, such a term encompasses any fluid pathway. Fluid chamber 310 includes an inlet port 312 and an outlet port 314. Within the fluid chamber 310 (e.g., along an interior surface of fluid chamber 310) is an electrokinetic film 320, such as an iron oxide film or a graphene layer. The electrokinetic film 320 is electrically coupled to an electronics system 330.

As downhole fluid passes through fluid chamber 310, the electrolytes in the downhole fluid interact with the electrokinetic film 320 to produce electrical current and a voltage (e.g., the generated voltage) (shown as (+) and (−)). Electronics system 330 can detect the voltage and determine a voltage parameter to be used to determine various characterizations of the downhole fluid. Oil and gas typically produces low to zero voltage using this system. Water based fluids can produce varying levels of voltages, depending on the quantity and the nature of the water based fluid. For example, pure water can result in one voltage level, and a water with ions or other substances can result in a different voltage level at the same concentration amount.

Figure 4:
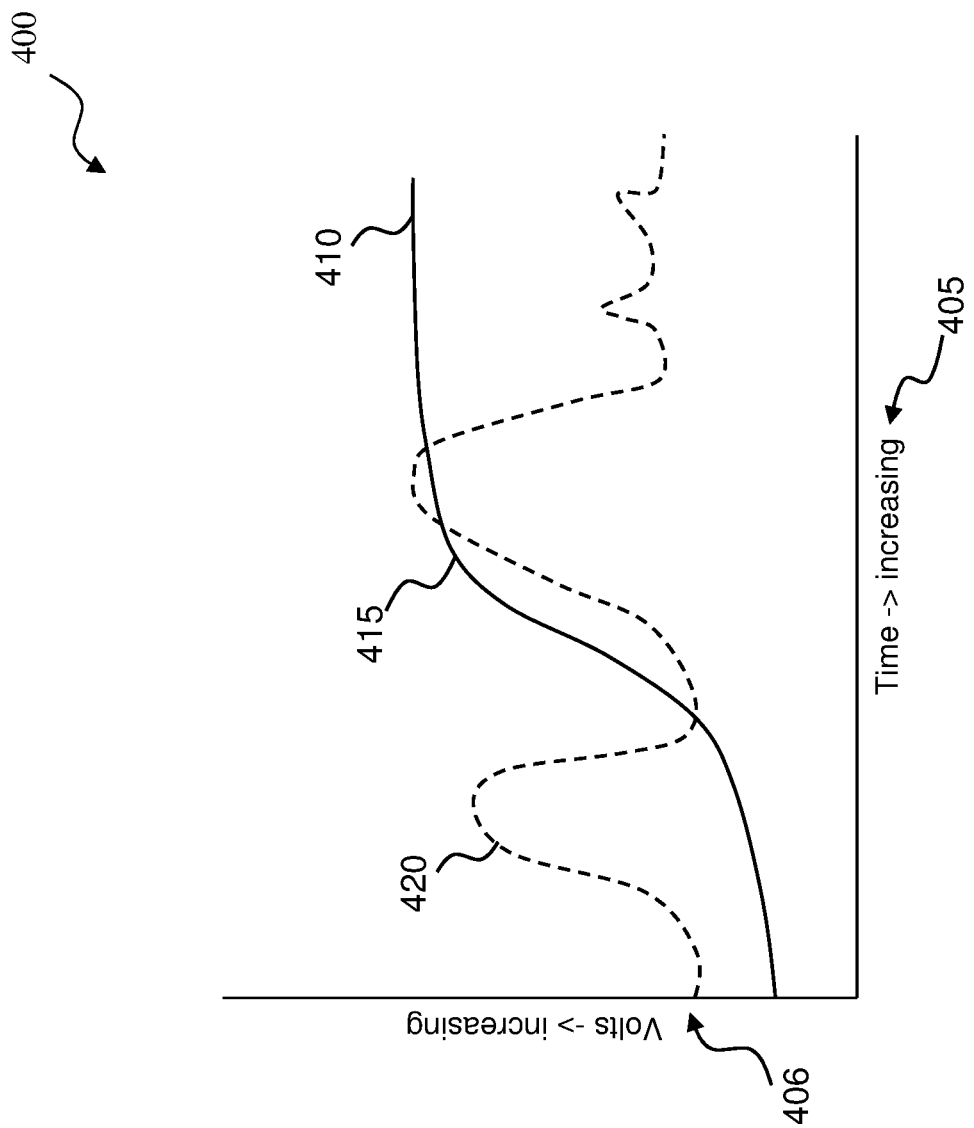
FIG. 4 is an illustration of a diagram of an example graph demonstrating fluid characterization.

FIG. 4 is an illustration of a diagram of an example graph 400 demonstrating fluid characterization. Graph 400 demonstrates one visual way the determined voltage parameters can be used to determine various downhole fluid characterizations. Graph 400 includes an x-axis 405 indicating the change over an increasing time, and includes a y-axis 406 indicating an increasing voltage detected.

Line 410 demonstrates an increase in the presence of water in a primarily oil downhole fluid. At point 415, the voltage parameter can indicate that a water cut threshold has been reached, as the amount of water has reached a stable maximum amount per fluid volume. Line 420 demonstrates a multiphase flow of downhole fluid. Each rise in voltage indicates the increased presence of water or other electrolyte substance in the downhole fluid. This could indicate a bubble of water passing through the fluid chamber or it could indicate the presence of other compounds or substances mixed in with the downhole fluid. Other analysis or additional voltage readings can be used to determine the makeup of the multiphase flow.

Figures 5A, 5B:
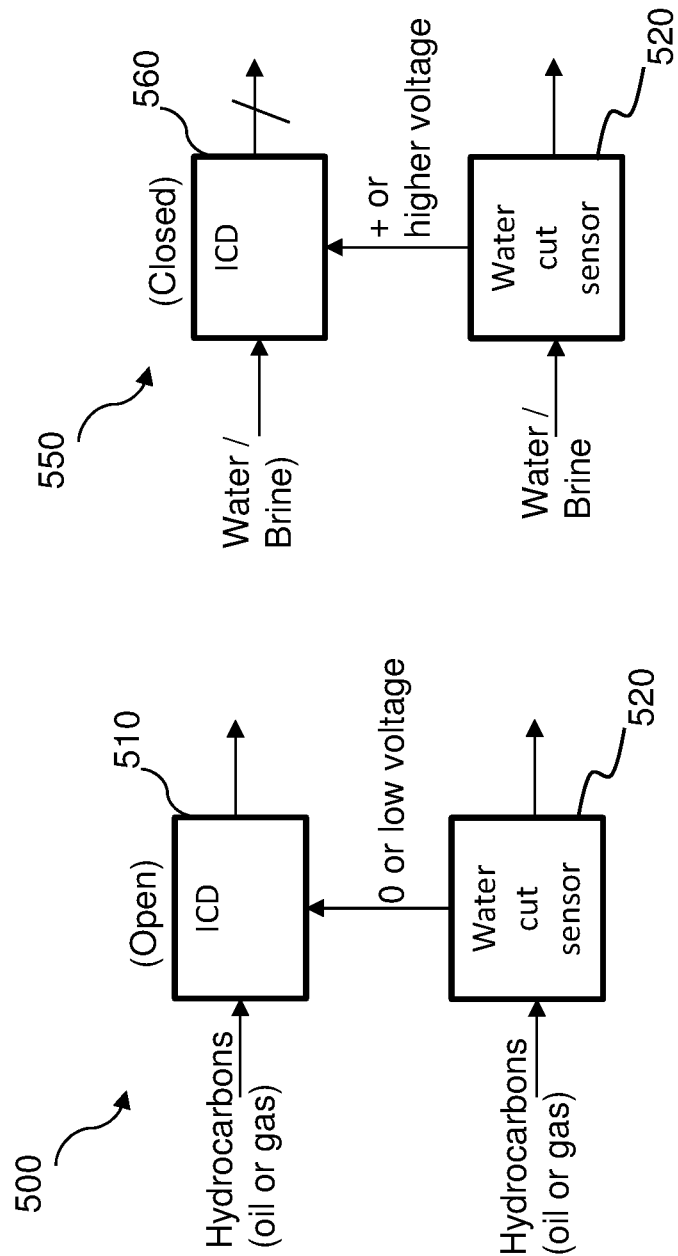
FIG. 5A is an illustration of a block diagram of an example water cut system and fluid flow control device as hydrocarbons flow through the fluid tubular.
FIG. 5B is an illustration of a block diagram of an example water cut system and fluid flow control device as water flows through the fluid tubular.

FIG. 5A is an illustration of a block diagram of an example water cut system 500 and fluid flow control device as hydrocarbons flow through the tubular. Water cut system 500 demonstrates a schematic when an OWD threshold is not exceeded. Water cut system 500 has a fluid flow control device 510 and a water cut sensor 520.

Water cut sensor 520, e.g., an OWD sensor, can be employed as part of a fluid flow control device, proximate a fluid flow control device, or with other tools, such as a hydraulic fracturing system, drilling tools, mud pumping system, or other tools, devices, or systems. Water cut sensor 520 can be located between an outer diameter of a structure or chamber, such as a tubular or fluid chamber, and an inner diameter of the structure or chamber. Water cut sensor 520 can be located wholly within the inner diameter of the structure or chamber. Water cut sensor 520 can be located wholly outside of the outer diameter of the structure or chamber.

Water cut sensor 520 includes an electrokinetic film within the inner diameter so that as downhole fluid flows through water cut sensor 520, a voltage can be detected. The detected voltage can be used to determine a voltage parameter. The voltage parameter can be used to determine the percentage of water present in the downhole fluid, and that information can be communicated to other systems, such as fluid flow control device 510. Water cut system 500 demonstrates that the voltage parameter indicates that a water cut threshold has not been exceeded so fluid flow control device 510 has its valves in an open position.

FIG. 5B is an illustration of a block diagram of an example water cut system 550 and fluid flow control device as water flows through the tubular. Water cut system 550 is similar to water cut system 500. Water cut system 550 includes a fluid flow control device 560 and water cut sensor 520. Water cut sensor 520 produces a voltage parameter that indicates the water cut threshold has been exceeded. That information is communicated to fluid flow control device 560 which closes one or more valves preventing or reducing the downhole fluid, now comprising enough water to exceed the water cut threshold, from continuing to flow along this path.

Figure 6:
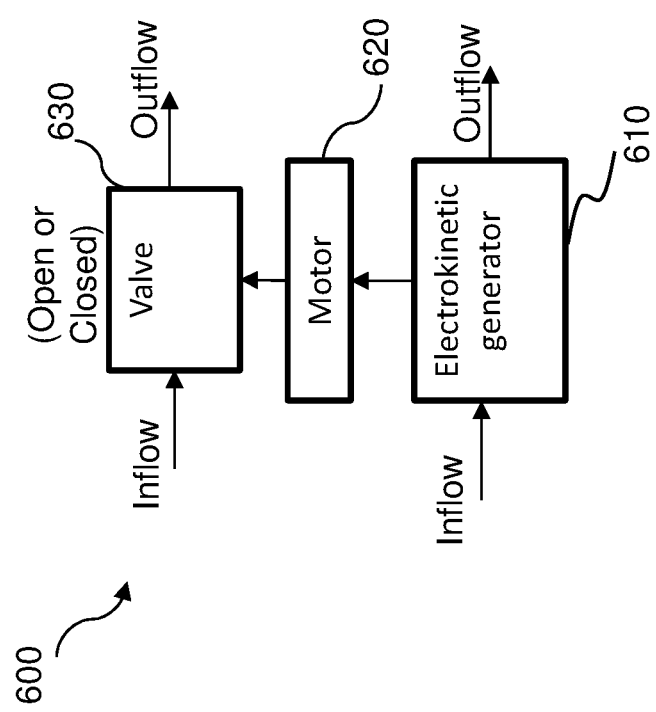
FIG. 6 is an illustration of a block diagram of an example electrokinetic system including an electrokinetic generator and fluid valve.

FIG. 6 is an illustration of a block diagram of an example electrokinetic system 600 including an electrokinetic generator and fluid valve. In some aspects, electrokinetic system 600 can be an AICD, an eICD, etc. Electrokinetic system 600 can use the electrical energy generated by downhole fluid flowing over the electrokinetic film to provide energy to one or more electric powered devices, such as valve motors. As the percentage of water increases in downhole fluid, the increase in electrical energy can be used to close one or more valves preventing additional water from entering the borehole system. For example, if a water breakthrough event is detected, such as by analyzing the voltage parameter, the valves can be closed using the energy provided by the energy generation system.

Electrokinetic system 600 includes an electrokinetic generator 610 (such as an energy generation system or an energy capture system) that can capture or store electrical energy, such as using batteries or capacitors. If a change in water content of the downhole fluid indicates (such as analyzing the voltage parameter) that a change in valve position is warranted, then electrokinetic generator 610 can provide energy to a motor 620 which can change the position of valve 630. Valve 630 can change from opened to close or closed to open, as well as anywhere in between, depending on the analysis of the voltage parameter.

Combined with water cut system 500 of FIG. 5A or water cut system 550 of FIG. 5B, an AICD or eICD system can be used to detect when a water cut threshold is exceeded by analyzing the change in the voltage parameter detected from the electrokinetic film and then change valve positions using the electrical energy generated by the same downhole fluid passing over the electrokinetic film. In some aspects, there can be more than one voltage detector to detect voltage changes at different locations within the fluid chamber or structure, as well as along the tubular.

Figure 7A:
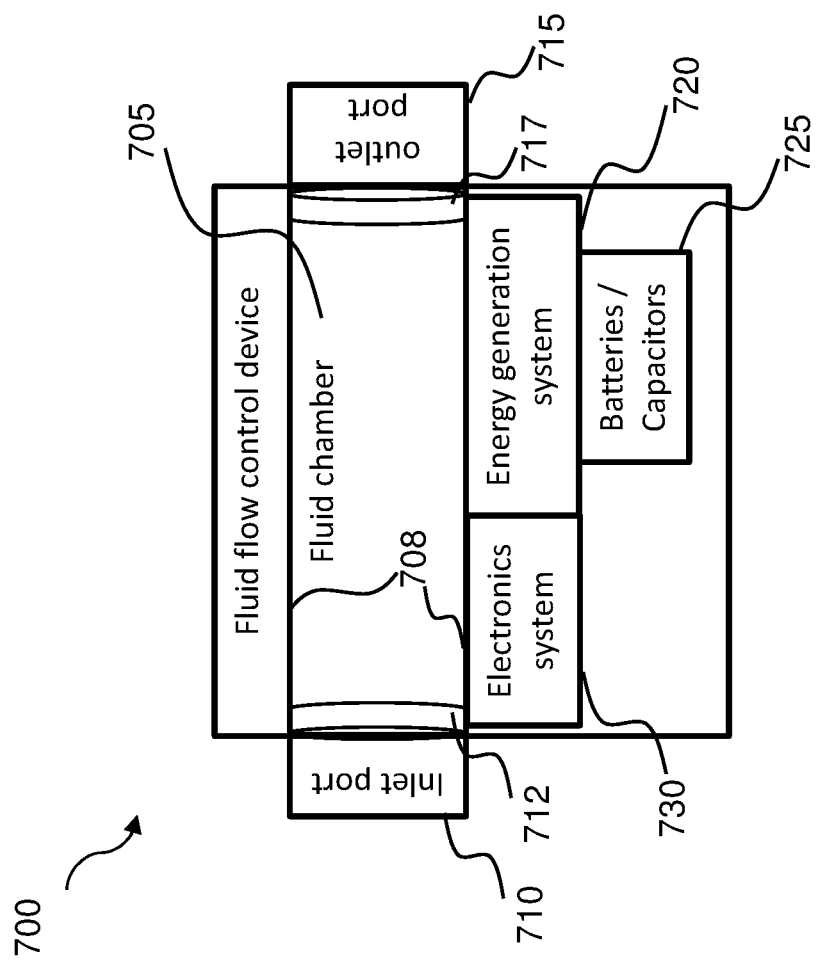
FIG. 7A is an illustration of a block diagram of an example fluid flow control device.

FIG. 7A is an illustration of a block diagram of an example fluid flow control device 700. Fluid flow control device 700 can be an AICD, an eICD, etc., or other types of fluid flow control devices. Fluid flow control device 700 has a fluid chamber 705. Fluid chamber 705 can be a chamber, structure, pipe, tubing, or other type of structure able to contain a downhole fluid. Fluid chamber 705 can be a small, contained object located with other downhole tools, or it can be a main tubular leading to a surface location.

On a first end of fluid chamber 705 is an inlet port 710 and a control valve 712. This allows downhole fluid to enter fluid chamber 705 when control valve 712 is in an open position. On a second end of fluid chamber 705 is an outlet port 715 and a control valve 717. This allows downhole fluid in fluid chamber 705 to exit when control valve 717 is in an open position.

Within the interior of fluid chamber 705 is an electrokinetic film 708. As downhole fluid passes over electrokinetic film 708, electrical energy can be generated and captured by an energy generation system 720. Energy generation system 720 can store the energy in an energy storage system 725, such as using batteries, capacitors, other storage systems, or combinations thereof. Energy generation system, 720 can provide energy to one or more motors, one or more valves, one or more electronics, (collectively, one or more devices or one or more tools), or one or more systems.

An electronics system 730 is coupled to the energy generation system 720 and the electrokinetic film 708. In some aspects, electronics system 730 includes voltage sensors to detect voltage changes as detected by electrokinetic film 708. In some aspects, external voltage sensors can be used and electrically coupled to electronics system 730. In some aspects, electronics system 730 can analyze the voltages received and determine a voltage parameter. In some aspects, electronics system 730 can direct operation of a fluid flow control device, such as directing a change in valve position of one or more valves using the voltage parameter. In some aspects, electronics system 730 can direct operation of energy generation system 720, such as prioritizing what devices receive energy or using the generated energy for operating electronics system 730 itself.

Figure 7B:
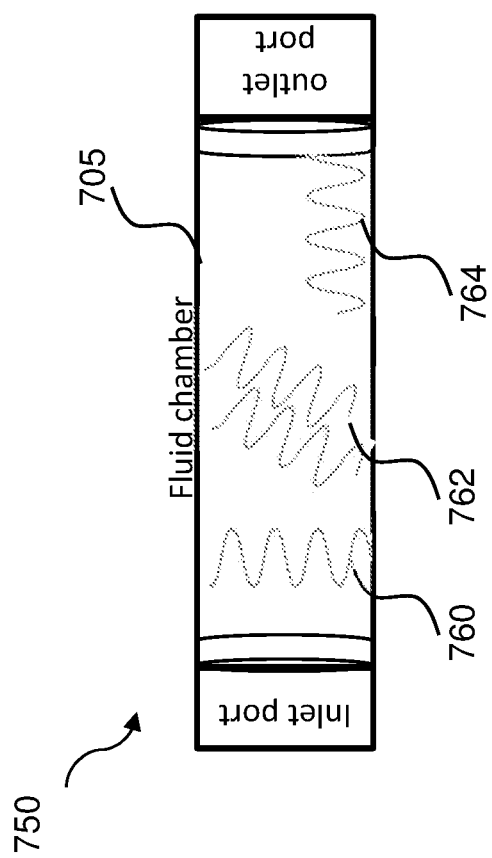
FIG. 7B is an illustration of a block diagram of an example folded electrokinetic film.

FIG. 7B is an illustration of a block diagram of an example folded electrokinetic film 750. Folded electrokinetic film 750 represents the same fluid chamber as fluid chamber 705 in FIG. 7A. In this demonstration, electrokinetic film 708 of FIG. 7A can be included using different types of structures, positions, or orientations within the interior of fluid chamber 705.

Pattern 760 demonstrates an electrokinetic film has been folded vertically within fluid chamber 705 to create more surface area, which can then generate more electrical energy. Pattern 762 demonstrates two electrokinetic films folded diagonally across the interior of fluid chamber 705. Pattern 764 demonstrates an electrokinetic film folded along the interior surface of fluid chamber 705. In some aspects, the electrokinetic film can cross the interior or cross the interior diameter of fluid chamber 705. One or more patterns can be used in various combinations. By using various patterns, voltage changes can be detected at various locations within fluid chamber 705 and each voltage parameter for each sensor location can be analyzed together to determine the composition of the downhole fluid, a percentage of water in the downhole fluid, or a fluid flow rate of the downhole fluid.

Figure 8:
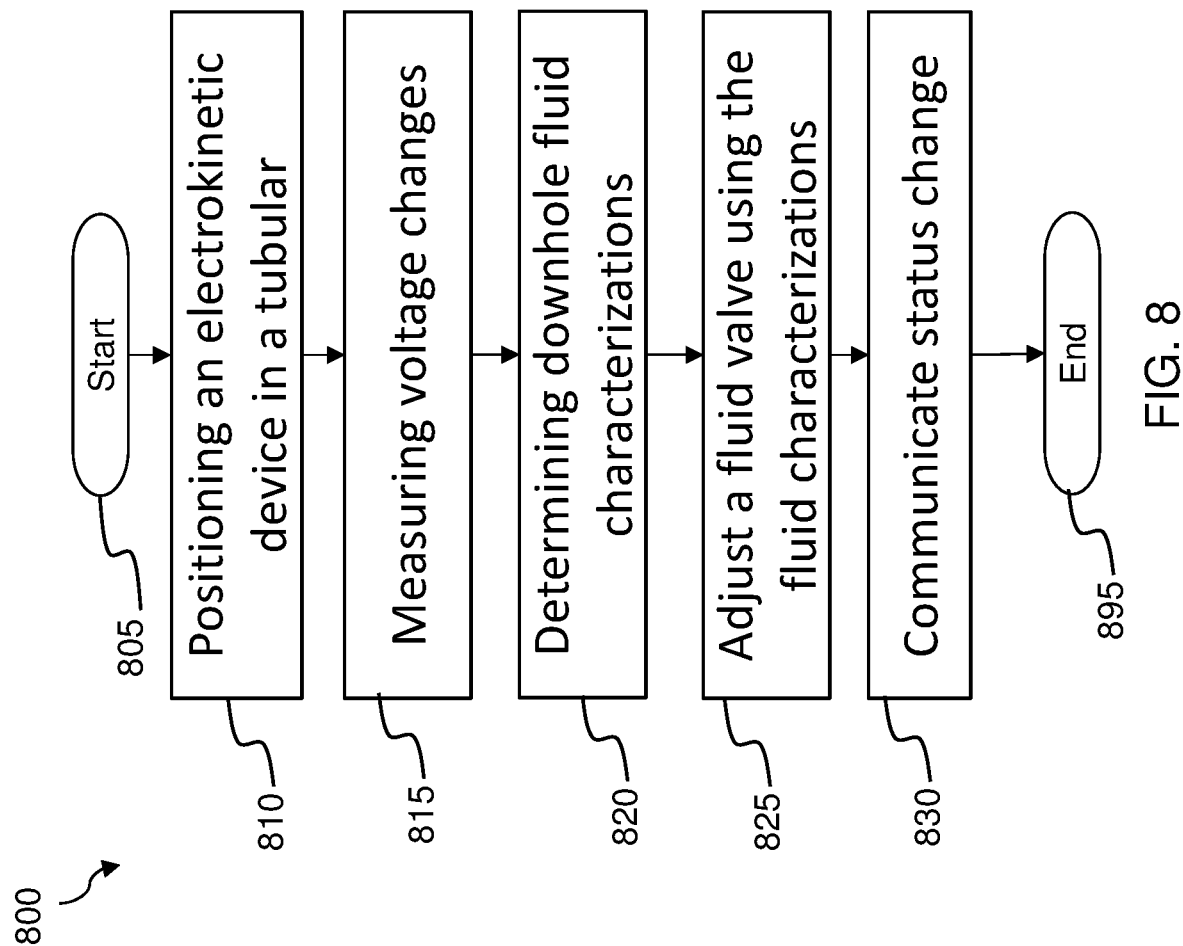
FIG. 8 is an illustration of a flow diagram of an example method for using an electrokinetic device in a fluid flow line.

FIG. 8 is an illustration of a flow diagram of an example method 800 for using an electrokinetic device in a tubular. Method 800 can be partially performed on a computing system, for example, electrokinetic fluid flow system 900 of FIG. 9 or electrokinetic fluid flow controller 1000 of FIG. 10. The computing system can be a downhole tool, a bottom hole assembly, a well site controller, a geo-steering system, a reservoir controller, a hydraulic fracturing controller, a data center, a cloud environment, a server, a laptop, a mobile device, a smartphone, a PDA, or other computing system capable of receiving the voltage data, input parameters, and capable of communicating with other computing systems. Method 800 can be partially encapsulated in software code or in hardware, for example, an application, code library, dynamic link library, module, function, RAM, ROM, and other software and hardware implementations. The software can be stored in a file, database, or other computing system storage mechanism. Method 800 can be partially implemented in software and partially in hardware.

Method 800 starts at a step 805 and proceeds to a step 810. In step 810, an electrokinetic device is positioned proximate to or in a tubular. For example, the electrokinetic device can be an AICD, an eICD, etc., or other types of fluid flow control devices, and the tubular can be piping, tubing, or a fluid chamber. The fluid is a downhole fluid, and can be a subterranean formation fluid being pumped to a surface location, a mud or injection fluid being pumped downhole, a hydraulic fracturing fluid, or other types of fluids found or located downhole a borehole, whether being pumped uphole, downhole, or otherwise moved through equipment to another location.

In a step 815, as the downhole fluid passes through the electrokinetic device, one or more sensors can be used to detect changes in voltage as generated by electrokinetic film located within the electrokinetic device. In a step 820, the changes in voltage can be used to determine one or more voltage parameters. The voltage parameters can be used to determine downhole fluid characterizations, for example, a fluid flow rate, a percentage of water, a water breakthrough, a water cut threshold exceeded, or other characterizations, such as an analysis of the types of ions present in the water.

In a step 825, the voltage parameters and the downhole fluid characterizations can be used as inputs to determine if a change in operations is needed, for example, opening or closing one or more valves to change the downhole fluid flow or to close off a section of a borehole. In a step 830, the voltage parameters or downhole fluid characterizations can be communicated to other systems, such as a well site controller, as operational decisions can be modified using the input information. For example, hydrocarbon extraction from a location downhole can be turned off in favor of other locations. While not illustrated in the method of FIG. 8, in one or more embodiments the energy generated by the electrokinetic film may be harvested to operate a related valve or other downhole device. Method 800 ends at a step 895.

Figure 9:
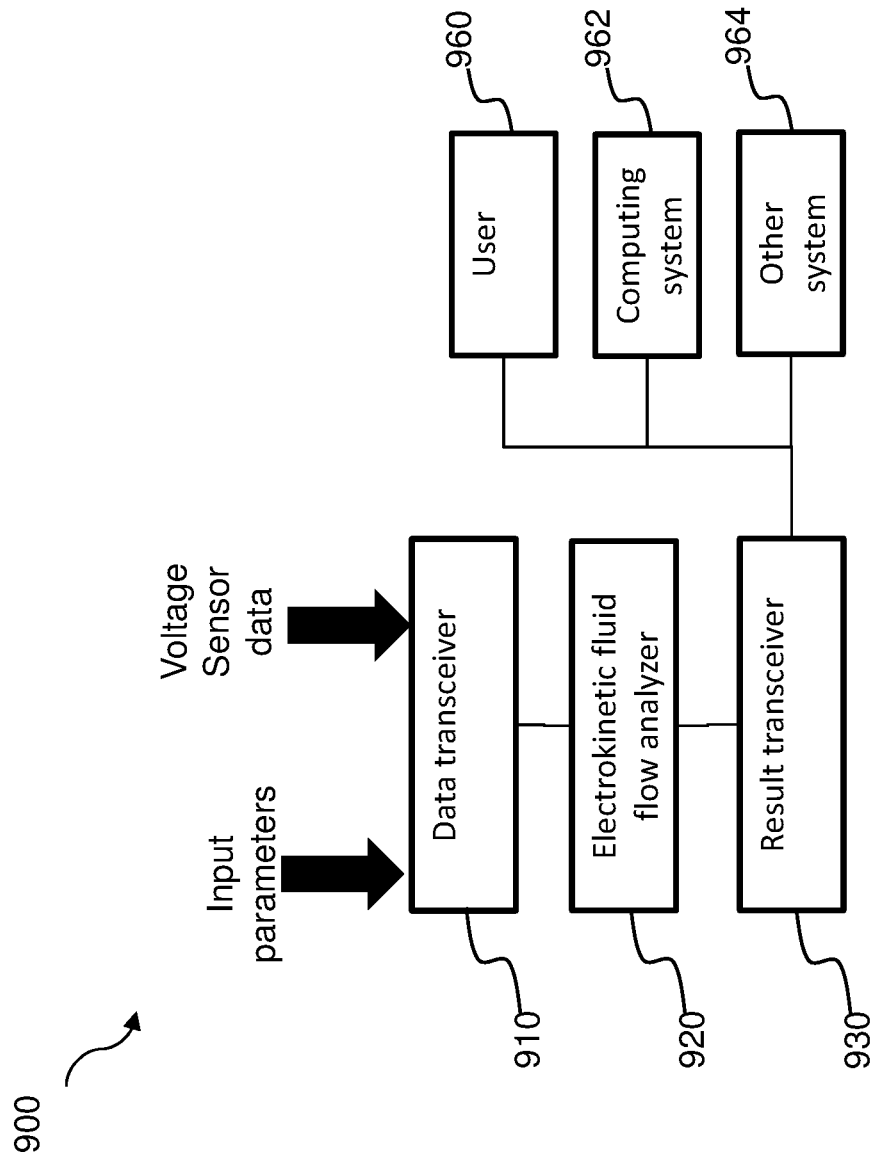
FIG. 9 is an illustration of a block diagram of an example electrokinetic fluid flow system.

FIG. 9 is an illustration of a block diagram of an example electrokinetic fluid flow system 900, which can be implemented in one or more computing systems, for example, a downhole tool, a bottom hole assembly, a drilling bit assembly, a hydraulic fracturing controller, a well site controller, a data center, cloud environment, server, laptop, smartphone, tablet, and other computing systems. In some aspects, electrokinetic fluid flow system 900 can be implemented using an electrokinetic fluid flow controller such as electrokinetic fluid flow controller 1000 of FIG. 10. Electrokinetic fluid flow system 900 can implement one or more methods of this disclosure, such as method 800 of FIG. 8. Electrokinetic fluid flow system 900 can be implemented using an electronics system, such as electronics system 730 of FIG. 7A.

Electrokinetic fluid flow system 900, or a portion thereof, can be implemented as an application, a code library, a dynamic link library, a function, a module, other software implementation, or combinations thereof. In some aspects, electrokinetic fluid flow system 900 can be implemented in hardware, such as a ROM, a graphics processing unit, or other hardware implementation. In some aspects, electrokinetic fluid flow system 900 can be implemented partially as a software application and partially as a hardware implementation. Electrokinetic fluid flow system 900 is a functional view of the disclosed processes and an implementation can combine or separate the described functions in one or more software or hardware systems.

Electrokinetic fluid flow system 900 includes a data transceiver 910, an electrokinetic fluid flow analyzer 920, and a result transceiver 930. The results, e.g., the potential alarms, the voltage parameters, the downhole fluid characterizations, the analysis, and the interim outputs from electrokinetic fluid flow analyzer 920 can be communicated to a data receiver, such as one or more of a user or user system 960, a computing system 962, or other processing or storage systems 964. The results can be used as input into other systems, such as to change a future stage of an operation plan by indicating a zone of the borehole should be shut off.

Data transceiver 910 can receive input parameters, such as parameters to direct the operation of the analysis implemented by electrokinetic fluid flow analyzer 920, such as a water cut threshold or other input parameters. In some aspects, data transceiver 910 can be part of electrokinetic fluid flow analyzer 920.

Result transceiver 930 can communicate one or more results, analysis, or interim outputs, to one or more data receivers, such as user or user system 960, computing system 962, storage system 964, e.g., a data store or database, or other related systems, whether located proximate result transceiver 930 or distant from result transceiver 930. Data transceiver 910, electrokinetic fluid flow analyzer 920, and result transceiver 930 can be, or can include, conventional interfaces configured for transmitting and receiving data. In some aspects, electrokinetic fluid flow analyzer 920 can be a machine learning system, such as applying learned analyzation models of voltage parameters to improve the determination of the composition of downhole fluid.

Figure 10:
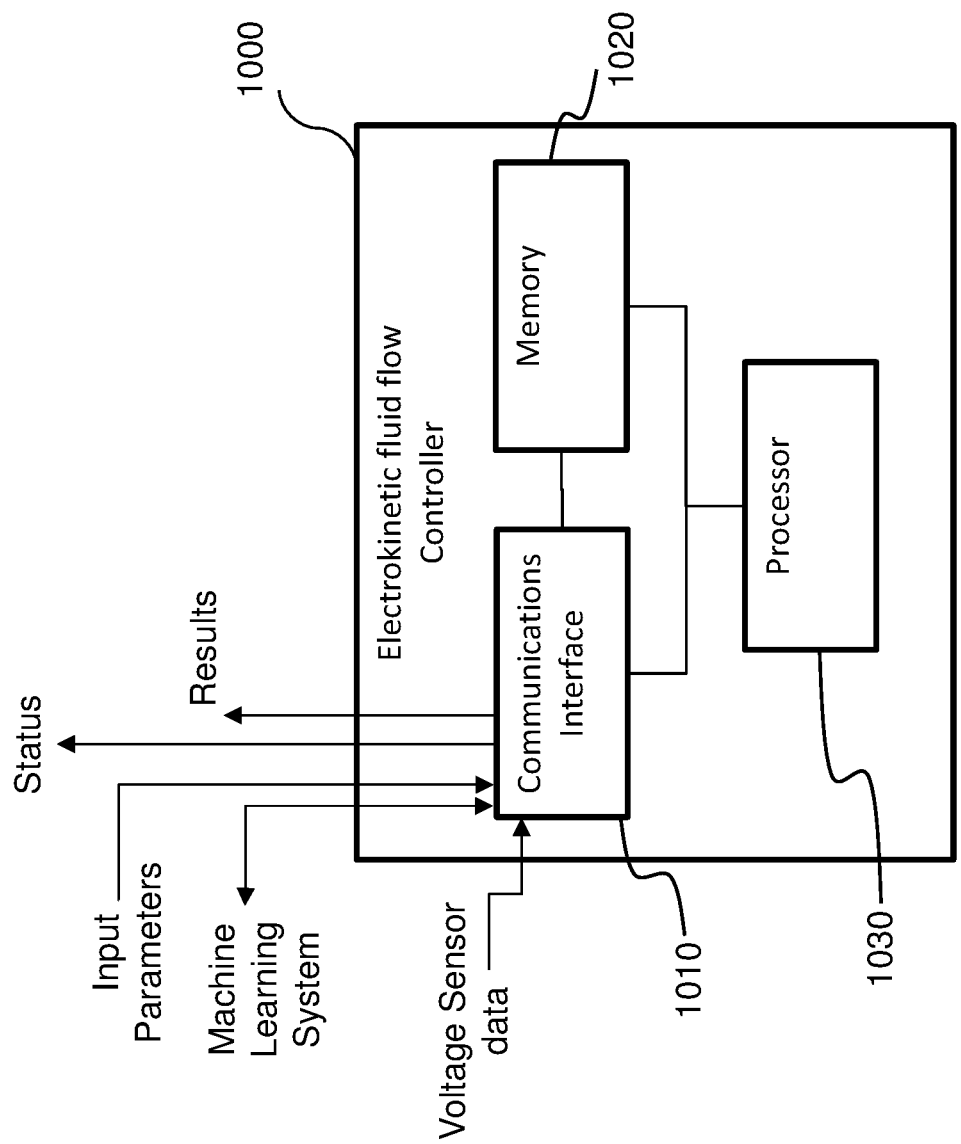
FIG. 10 is an illustration of a block diagram of an example of an electrokinetic fluid flow controller according to the principles of the disclosure.

Electrokinetic fluid flow analyzer 920 (e.g., one or more analyzation processors such as processor 1030 of FIG. 10) can implement the analysis and algorithms as described herein utilizing the sensor data, the input parameters, and other algorithms that have been made available.

A memory or data storage of electrokinetic fluid flow analyzer 920 can be configured to store the processes and algorithms for directing the operation of electrokinetic fluid flow analyzer 920. Electrokinetic fluid flow analyzer 920 can also include one or more processors that are configured to operate according to the analysis operations and algorithms disclosed herein, and an interface to communicate (transmit and receive) data.

FIG. 10 is an illustration of a block diagram of an example of an electrokinetic fluid flow controller 1000 according to the principles of the disclosure. Electrokinetic fluid flow controller 1000 can be stored on a single computer or multiple computers. The various components of electrokinetic fluid flow controller 1000 can communicate via wireless or wired conventional connections. A portion or a whole of electrokinetic fluid flow controller 1000 can be located at one or more locations and other portions of electrokinetic fluid flow controller 1000 can be located on a computing device or devices located at a surface location. In some aspects, electrokinetic fluid flow controller 1000 can be wholly located at a surface or distant location. In some aspects, electrokinetic fluid flow controller 1000 can be part of another system, and can be integrated into a single device, such as a part of a borehole operation system, a well site controller, or other borehole system. In some aspects, electrokinetic fluid flow controller 1000 can include an energy generation system or an energy capture system, such as electrokinetic generator 610 of FIG. 6. In some aspects, electrokinetic fluid flow controller 1000 can include an electronics system, such as electronics system 730 of FIG. 7A.

Electrokinetic fluid flow controller 1000 can be configured to perform the various functions disclosed herein including receiving input parameters, voltage sensor data, and generating results from an execution of the methods and processes described herein, such as generating a voltage parameter and downhole fluid characterizations. Electrokinetic fluid flow controller 1000 includes a communications interface 1010, a memory 1020, and a processor 1030.

Communications interface 1010 is configured to transmit and receive data. For example, communications interface 1010 can receive the input parameters and voltage sensor data. Communications interface 1010 can transmit the results, data from the input parameters, or interim outputs. In some aspects, communications interface 1010 can transmit a status, such as a success or failure indicator of electrokinetic fluid flow controller 1000 regarding receiving the various inputs, transmitting the generated results, or producing the results.

In some aspects, communications interface 1010 can receive input parameters from a machine learning system, for example, where the voltage sensor data is processed using one or more filters and algorithms and the machine learning system uses prior learned analyzation models to improve the determination of the downhole fluid characterizations and voltage parameters.

In some aspects, the machine learning system can be implemented by processor 1030 and perform the operations as described by electrokinetic fluid flow analyzer 920. Communications interface 1010 can communicate via communication systems used in the industry. For example, wireless or wired protocols can be used. Communication interface 1010 is capable of performing the operations as described for data transceiver 910 and result transceiver 930 of FIG. 9.

Memory 1020 can be configured to store a series of operating instructions that direct the operation of processor 1030 when initiated, including the code representing the algorithms for determining and processing the collected data. Memory 1020 is a non-transitory computer-readable medium. Multiple types of memory can be used for data storage and memory 1020 can be distributed.

Processor 1030 can be configured to produce the results (e.g., generating the evaluation algorithm), one or more interim outputs, and statuses utilizing the received inputs. Processor 1030 can be configured to direct the operation of electrokinetic fluid flow controller 1000. Processor 1030 includes the logic to communicate with communications interface 1010 and memory 1020, and perform the functions described herein. Processor 1030 is capable of performing or directing the operations as described by electrokinetic fluid flow analyzer 920 of FIG. 9. Processor 1030 can be one or more processors and be of one or more types of processors.

In the drawings and descriptions that follow, like parts are typically marked throughout the specification and drawings with the same reference numerals, respectively. The drawn figures are not necessarily to scale. Certain features of the disclosure may be shown exaggerated in scale or in somewhat schematic form and some details of certain elements may not be shown in the interest of clarity and conciseness. The present disclosure may be implemented in aspects of different forms.

Specific aspects are described in detail and are shown in the drawings, with the understanding that the present disclosure is to be considered an exemplification of the principles of the disclosure, and is not intended to limit the disclosure to that illustrated and described herein. It is to be fully recognized that the different teachings of the aspects discussed herein may be employed separately or in any suitable combination to produce desired results.

Unless otherwise specified, use of the terms "connect," "engage," "couple," "attach," or any other like term describing an interaction between elements is not meant to limit the interaction to direct interaction between the elements and may also include indirect interaction between the elements described. Unless otherwise specified, use of the terms "up," "upper," "upward," "uphole," "upstream," or other like terms shall be construed as generally away from the bottom, terminal end of a well, regardless of the wellbore orientation; likewise, use of the terms "down," "lower," "downward," "downhole," or other like terms shall be construed as generally toward the bottom, terminal end of a well, regardless of the wellbore orientation. Use of any one or more of the foregoing terms shall not be construed as denoting positions along a perfectly vertical axis. In some instances, a part near the end of the well can be horizontal or even slightly directed upwards. Unless otherwise specified, use of the term "subterranean formation" shall be construed as encompassing both areas below exposed earth and areas below earth covered by water such as ocean or fresh water.

A portion of the above-described apparatus, systems or methods may be embodied in or performed by various analog or digital data processors, wherein the processors are programmed or store executable programs of sequences of software instructions to perform one or more of the steps of the methods. A processor may be, for example, a programmable logic device such as a programmable array logic (PAL), a generic array logic (GAL), a field programmable gate array (FPGA), or another type of computer processing device (CPD). The software instructions of such programs may represent algorithms and be encoded in machine-executable form on non-transitory digital data storage media, e.g., magnetic or optical disks, random-access memory (RAM), magnetic hard disks, flash memories, or read-only memory (ROM), to enable various types of digital data processors or computers to perform one, multiple or all of the steps of one or more of the above-described methods, or functions, systems or apparatuses described herein.

Portions of disclosed examples or aspects may relate to computer storage products with a non-transitory computer-readable medium that has program code thereon for performing various computer-implemented operations that embody a part of an apparatus, device or carry out the steps of a method set forth herein. Non-transitory used herein refers to all computer-readable media except for transitory, propagating signals. Examples of non-transitory computer-readable media include, but are not limited to: magnetic media such as hard disks, floppy disks, and magnetic tape; optical media such as CD-ROM disks; magneto-optical media such as floppy disks; and hardware devices that are specially configured to store and execute program code, such as ROM and RAM devices. Configured or configured to means, for example, designed, constructed, or programmed, with the necessary logic or features for performing a task or tasks. Examples of program code include both machine code, such as produced by a compiler, and files containing higher-level code that may be executed by the computer using an interpreter.

In interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Those skilled in the art to which this application relates will appreciate that other and further additions, deletions, substitutions, and modifications may be made to the described aspects. It is also to be understood that the terminology used herein is for the purpose of describing particular aspects only, and is not intended to be limiting, since the scope of the present disclosure will be limited only by the claims. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, a limited number of the exemplary methods and materials are described herein.

Each of aspects in the SUMMARY section can have one or more of the following additional elements in combination. Element 1: an electronics system able to determine the voltage parameter at one or more locations within the fluid chamber using the generated voltage. Element 2: wherein the fluid flow control device is one of an AICD, or an eICD. Element 3: a valve set, the valve set containing one or more valves whose position is set using the voltage parameter Element: Element 4: wherein the one or more valves control a flow of the downhole fluid through the inlet port, the outlet port, or within the fluid chamber. Element 5: an energy generation system, wherein the electrokinetic film generates electrical energy that is captured by the energy generation system. Element 6: an energy storage system, capable of storing the electrical energy captured by the energy generation system, wherein the energy storage system is batteries or capacitors. Element 7: wherein the energy generation system provides energy to one or more valve motors. Element 8: an electronics system able to determine a voltage parameter at one or more measuring locations within the fluid chamber using the generated voltage. Element 9: wherein the voltage parameter changes in proportion to an amount of water in the downhole fluid. Element 10: where the downhole fluid is one or more of a gas, an oil, a water, a brine, a drilling mud, a fracturing fluid, or an injection fluid. Element 11: wherein the electronics system determines a percentage of water in the downhole fluid. Element 12: wherein the electronics system determines the voltage parameter in real-time from the generated voltage. Element 13: wherein the electronics system detects a change in a composition of the downhole fluid utilizing variations of the voltage parameter occurring at the one or more measuring locations within the fluid chamber. Element 14: wherein the electronics system detects an OWD and communicates the OWD. Element 15: wherein the electronics system directs an operation of one or more valves of the fluid flow control device using the OWD. Element 16: an energy capture system to capture an electrical energy generated by the downhole fluid flowing over a surface of the electrokinetic film, wherein the energy capture system utilizes one or more batteries or one or more capacitors. Element 17: wherein the energy capture system provides energy to one or more valves of the fluid flow control device. Element 18: wherein the energy capture system provides energy to one or more devices, one or more tools, or one or more computing systems external to the well system. Element 19: wherein the electrokinetic film is folded to create a second surface area of the electrokinetic film that is greater than a first surface area of an interior of the fluid chamber. Element 20: the electrical energy generated is increased due to the second surface area over the first surface area. Element 21: wherein a fluid flow rate is determined by analyzing variations of the voltage as the downhole fluid flows over the electrokinetic film. Element 22: wherein the borehole is part of a drilling borehole system, an injection borehole system, a hydraulic fracturing borehole system, a production borehole system, or a completed borehole system. Element 23: wherein the one or more downhole fluid characterizations are one or more of a fluid flow rate, a percentage of water in the downhole fluid, or an OWD threshold. Element 24: capturing electrical energy generated by the downhole fluid flowing past the electrokinetic film. Element 25: wherein the electrical energy is stored in one or more batteries or capacitors, or is used by a component of the fluid flow control device or a device external to the fluid flow control device.

What is claimed is:

1. A fluid flow control device for use with a downhole tool located in a borehole, comprising:
    an inlet port, allowing a downhole fluid of the borehole to flow into the fluid flow control device;
    an outlet port, allowing the downhole fluid to flow out of the fluid flow control device; and
    a fluid chamber positioned between the inlet port and the outlet port, wherein an electrokinetic film is located within the fluid chamber and is capable of generating a voltage as the downhole fluid flows over the electrokinetic film, and a voltage parameter can be determined from the generated voltage.

2. The fluid flow control device as recited in claim 1, further comprising:
    an electronics system able to determine the voltage parameter at one or more locations within the fluid chamber using the generated voltage.

3. The fluid flow control device as recited in claim 1, wherein the fluid flow control device is one of an autonomous inflow control device (AICD), or an electronic ICD (eICD).

4. The fluid flow control device as recited in claim 1, further comprising:
    a valve set, the valve set containing one or more valves whose position is set using the voltage parameter and wherein the one or more valves control a flow of the downhole fluid through the inlet port, the outlet port, or within the fluid chamber.

5. The fluid flow control device as recited in claim 1, further comprising:
    an energy generation system, wherein the electrokinetic film generates electrical energy that is captured by the energy generation system.

6. The fluid flow control device as recited in claim 5, further comprising:
    an energy storage system, capable of storing the electrical energy captured by the energy generation system, wherein the energy storage system is batteries or capacitors.

7. The fluid flow control device as recited in claim 5, wherein the energy generation system provides energy to one or more valve motors.

8. A well system, comprising:
    a borehole formed through a subterranean formation;
    a tubing string positioned within the borehole; and
    a fluid flow control device coupled to the tubing string, the fluid flow control device including:
        an inlet port, allowing a downhole fluid of the borehole to flow into the fluid flow control device;

an outlet port, allowing the downhole fluid to flow out of the fluid flow control device; and a fluid chamber positioned between the inlet port and the outlet port, wherein an electrokinetic film is located within the fluid chamber and is capable of generating a voltage as the downhole fluid flows over the electrokinetic film.

9. The well system as recited in claim 8, further comprising:

an electronics system able to determine a voltage parameter at one or more measuring locations within the fluid chamber using the generated voltage.

10. The well system as recited in claim 9, wherein the voltage parameter changes in proportion to an amount of water in the downhole fluid, where the downhole fluid is one or more of a gas, an oil, a water, a brine, a drilling mud, a fracturing fluid, or an injection fluid.

11. The well system as recited in claim 9, wherein the electronics system determines a percentage of water in the downhole fluid.

12. The well system as recited in claim 9, wherein the electronics system determines the voltage parameter in real-time from the generated voltage.

13. The well system as recited in claim 9, wherein the electronics system detects a change in a composition of the downhole fluid utilizing variations of the voltage parameter occurring at the one or more measuring locations within the fluid chamber.

14. The well system as recited in claim 9, wherein the electronics system detects an on-line water determination (OWD) and communicates the OWD.

15. The well system as recited in claim 14, wherein the electronics system directs an operation of one or more valves of the fluid flow control device using the OWD.

16. The well system as recited in claim 8, further comprising:

an energy capture system to capture an electrical energy generated by the downhole fluid flowing over a surface of the electrokinetic film, wherein the energy capture system utilizes one or more batteries or one or more capacitors.

17. The well system as recited in claim 16, wherein the energy capture system provides energy to one or more valves of the fluid flow control device.

18. The well system as recited in claim 16, wherein the energy capture system provides energy to one or more devices, one or more tools, or one or more computing systems external to the well system.

19. The well system as recited in claim 16, wherein the electrokinetic film is folded to create a second surface area of the electrokinetic film that is greater than a first surface area of an interior of the fluid chamber, and the electrical energy generated is increased due to the second surface area over the first surface area.

20. The well system as recited in claim 8, wherein a fluid flow rate is determined by analyzing variations of the voltage as the downhole fluid flows over the electrokinetic film.

21. The well system as recited in claim 8, wherein the borehole is part of a drilling borehole system, an injection borehole system, a hydraulic fracturing borehole system, a production borehole system, or a completed borehole system.

22. A method, comprising:

positioning a fluid flow control device coupled to tubing string within a borehole formed through a subterranean formation, the fluid flow control device including:

an inlet port, allowing a downhole fluid of the borehole to flow into the fluid flow control device;

an outlet port, allowing the downhole fluid to flow out of the fluid flow control device;

a fluid chamber positioned between the inlet port and the outlet port, wherein an electrokinetic film is located in an interior of the fluid chamber and is capable of generating a voltage as the downhole fluid flows over the electrokinetic film; and an electronics system able to determine one or more voltage parameters at one or more measuring locations within the fluid chamber using the generated voltage;

analyzing the one or more voltage parameters using the electronics system; and determining a one or more downhole fluid characterizations using the one or more voltage parameters.

23. The method as recited in claim 22, wherein the one or more downhole fluid characterizations are one or more of a fluid flow rate, a percentage of water in the downhole fluid, or an on-line water determination (OWD) threshold.

24. The method as recited in claim 22, further comprising:

capturing electrical energy generated by the downhole fluid flowing past the electrokinetic film, wherein the electrical energy is stored in one or more batteries or capacitors, or is used by a component of the fluid flow control device or a device external to the fluid flow control device.

* * * * *